United States Patent [19]

D'Amico et al.

[11] 4,239,527
[45] Dec. 16, 1980

[54] 2-(PYRIDYLTHIO)PYRIDINE-N-OXIDES

[75] Inventors: John J. D'Amico, Olivette; David E. Schafer, Creve Coeur, both of Mo.

[73] Assignee: Monsanto Company, St. Louis, Mo.

[21] Appl. No.: 963,487

[22] Filed: Nov. 24, 1978

[51] Int. Cl.$^3$ .............................................. A01N 43/40
[52] U.S. Cl. ........................................ 71/94; 47/57.6; 71/118; 546/261
[58] Field of Search ............................... 71/94; 47/57.6

[56] References Cited

U.S. PATENT DOCUMENTS

| | | | |
|---|---|---|---|
| 2,826,585 | 3/1958 | Cislak | 260/294.8 |
| 3,155,671 | 11/1964 | D'Amico | 260/294.8 |
| 3,207,760 | 9/1965 | Brown et al. | 260/294.8 |
| 3,295,946 | 1/1967 | D'Amico | 71/94 |
| 3,495,969 | 2/1970 | Driscoll | 71/94 |
| 3,810,752 | 5/1974 | Wilcox | 71/94 |
| 4,049,665 | 9/1977 | Douglass | 260/294.8 S |

*Primary Examiner*—Catherine L. Mills
*Attorney, Agent, or Firm*—Patricia A. Coburn; Donald W. Peterson

[57] ABSTRACT

The invention relates to 2-(pyridylthio)pyridine-N-oxides and their use in reducing the herbicidal injury to sorghum due to the application thereto of various herbicides.

12 Claims, No Drawings

2-(PYRIDYLTHIO)PYRIDINE-N-OXIDES

This invention relates to novel 2-(pyridylthio)pyridine-N-oxides and halogenated derivatives thereof as well as their use in compositions and methods for reducing herbicidal injury. More specifically, the invention relates to novel compositions and methods for reducing injury to crop plants by herbicides, such as acetanilides, which comprises treating the crop plant locus or the seed of the crop plant with an effective amount of a compound having the formula

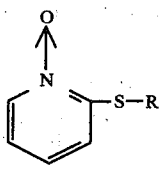
(I)

wherein R is 2-pyridyl or 2-pyridyl substituted with from one to four halogen atoms, especially chloro.

BACKGROUND OF THE INVENTION

Acetanilide herbicides are very useful for controlling certain weeds, especially grasses, in the presence of growing crops. However, many of the acetanilide herbicides injure certain crop plants slowing growth and development at application rates necessary to stunt or kill the weeds. Accordingly, some of the acetanilide herbicides cannot be used for controlling weeds in the presence of certain crops. Obviously, a safening agent consisting of a composition that could be used to treat the seed of the crop plant, the crop plant locus or the crop plant itself, resulting in a reduction of injury due to application of the herbicide without a corresponding reduction of herbicidal action on the weed, would be quite beneficial.

DESCRIPTION OF THE INVENTION

In accordance with the novel aspects of the present invention, injury to crop plants, such as sorghum, due to application thereto of acetanilide herbicides, such as 2-chloro-2',6'-diethyl-N-(methoxymethyl)acetanilide (hereinafter referred to by its common name, alachlor), 2-chloro-2',6'-diethyl-N-(butoxymethyl)acetanilide (hereinafter referred to by its common name, butachlor), 2-chloro-N-isopropylacetanilide (hereinafter referred to by its common name, propachlor), N-(ethoxymethyl)-N-(2-ethyl-6-methyl-1-cyclohexen-1-yl)-2-chloroacetamide, N-(ethoxymethyl)-N-(2,5-dimethyl-1-cyclopenten-1-yl)-2-chloroacetamide, 2-chloro-N-(2-methoxy-1-methylethyl)-6'-ethyl-o-acetotoluidide and 2-chloro-N-(ethoxymethyl)-6'-ethyl-o-acetotoluidide, may be reduced without a corresponding reduction in injury to the weeds by application to the crop plant locus or the seed of the crop plant prior to planting of an effective amount of a safening agent comprising a compound of Formula (I) above.

The 2-(pyridylthio)pyridine-N-oxides of the present invention can be prepared by reaction of the sodium salt of 2-mercaptopyridine-N-oxide with a halogenated pyridine, especially 2-chloropyridine, in accordance with the following equation.

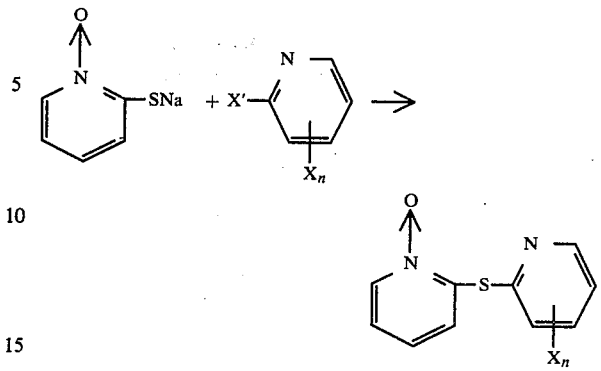

In the above equation, X represents halogen, X' represents halogen and n is an integer from 0 to 4. By way of example, 2-(3,4,5,6-tetrachloro-2-pyridylthio)pyridine-N-oxide was prepared as follows.

To a stirred slurry containing 18.3 grams (0.11 mol) of 90% sodium salt of 2-mercaptopyridine-N-oxide in 200 ml. of ethyl alcohol, 25.2 grams (0.1 mol) of pentachloropyridine is added in one portion. The stirred reaction mixture is heated at reflux for six hours and then at 25°–30° C. for 48 hours. After the addition of 800 ml. of water, stirring is continued at 25°–30° C. for 30 minutes. The solid is collected by filtration, washed with water until neutral to litmus and air-dried at 25°–30° C. The product, m.p. 163°–165° C., is obtained in 96.5% yield. After recrystallization from toluene, it melted at 165°–167° C.

Anal. Calc'd. for $C_{10}H_{14}Cl_4N_2OS$: C, 35.12; H, 1.18; Cl, 41.46; N, 8.18; S, 9.37. Found: C, 35.21; H, 1.23; Cl, 41.38; N, 8.27; S, 9.29.

As noted, the compounds of the invention are useful as safening agents in reducing herbicidal injury to sorghum plants.

The amount of safening agent employed in the method and compositions of the invention will vary depending upon the particular herbicide with which the agent is employed, the rate of application of the herbicide, the crop to be protected as well as the manner of application of the safening agent. In each instance, the amount employed is a safening effective amount, i.e., the amount which reduces crop injury by the acetanilide herbicide.

The safening agent may be applied to the plant locus in a mixture with the herbicide, sequentially or it may be applied directly to the seed of the crop plant. By application to the "plant locus" is meant application to the plant growing medium, such as the soil, as well as the seeds, emerging seedlings, roots, stems, leaves, flowers, fruits or other plant parts.

The amount of herbicide employed is well within the skill of the art and is disclosed in various patents. Propachlor and its herbicidal use is disclosed in U.S. Pat. No. 2,863,752 and U.S. Pat. No. 26,961. Alachlor, butachlor and 2-chloro-N-(ethoxymethyl)-6'-ethyl-o-acetotoluidide and their herbicidal use are disclosed in U.S. Pat. Nos. 3,442,945 and 3,547,620. U.S. Pat. No. 3,937,730 discloses and claims 2-chloro-N-(2-methoxy-1-methylethyl)-6'-ethyl-o-acetotoluidide. The herbicidal use of N-(ethoxymethyl)-N-(2-ethyl-6-methyl-1-cyclohexen-1-yl)-2-chloroacetamide and N-(ethoxymethyl)-N-(2,5-dimethyl-1-cyclopenten-1-yl)-2-chloroacetamide is disclosed in application Ser. No. 897,472, filed Apr. 18, 1978 by John P. Chupp.

2-(3,4,5,6-tetrachloro-2-pyridylthio)pyridine-N-oxide was tested for its properties as a safening agent as follows.

EXAMPLE 1

A good grade of top soil is placed in a container and compacted to a depth of approximately 1.27 cm. from the top of said container. A predetermined number of sorghum seeds to be tested are placed on top of the soil. A quantity of soil sufficient to substantially fill the container is measured and placed in a second container. A measured quantity of the safening agent dispersed or dissolved in a suitable carrier is applied to the soil in the second container. A measured quantity of the acetanilide herbicide dispersed or dissolved in a suitable carrier is then sprayed on the soil already treated with the safening agent. The soil containing the safening agent and herbicide is thoroughly mixed. This mixing is sometimes referred to as incorporation of the herbicide and safening agent into the soil. The mixing or incorporation provides a substantially uniform distribution of the safening agent and herbicide throughout the soil. The seeds are covered with the soil containing the safening agent and acetanilide herbicide and the pots are leveled. The pots are then placed on a sand bench in the greenhouse and watered from below as needed. The plants are observed at the end of approximately 21 days and the results in terms of percent inhibition of each seed lot are recorded. For each test series, a pot is also prepared containing no acetanilide herbicide and no safening agent as a control. Additionally, for each test, pots are prepared with soil covering the seed containing no acetanilide herbicide and only the measured amount of safening agent being incorporated into the soil covering the seeds to ascertain any herbicidal effect of the safening agent alone. For each series of tests, the herbicidal effect of the acetanilide herbicide is observed from pots treated with the same quantity of herbicide alone. The "safening effect" is determined by adding the herbicidal effect of the acetanilide herbicide when applied alone to the herbicidal effect of the safening agent when applied alone (in no instance, however, will this sum be greater than 100) and substracting from that the herbicidal effect obtained when both the herbicide and safening agent are incorporated into the soil as discussed above. The safening effect when 2.24 kilograms per hectare of alachlor was utilized as the herbicide and 8.96 kilograms per hectare of safening agent was used was 29, which meant that the sorghum was safened by $(94+0-65)/94\times100$ or 30.8%. When 4.48 kilograms per hectare of butachlor was used as the herbicide and 8.96 kilograms per hectare of safening agent was used, the safening effect was 45, which meant that the sorghum was safened by $(75-30)/75\times100$, or 60%.

EXAMPLE 2

The procedure of Example 1 was repeated utilizing different rates of alachlor and 8.96 kilograms per hectare of 2-(3,4,5,6-tetrachloro-2-pyridylthio)pyridine-N-oxide as the safening agent. Table I, below, summarizes the results of said test.

TABLE I

| Herbicide Rate (kg/ha) | Safening Agent Rate (kg/ha) | Percent Inhibition of Sorghum | Safening Effect | Percent Safened |
|---|---|---|---|---|
| 0.07 | 0 | 13 | | |
| 0.28 | 0 | 58 | | |
| 1.12 | 0 | 99 | | |
| 4.48 | 0 | 99 | | |
| 0.07 | 8.96 | 0 | 13 | 100 |
| 0.28 | 8.96 | 5 | 53 | 91.3 |
| 1.12 | 8.96 | 20 | 79 | 79.7 |
| 4.48 | 8.96 | 75 | 24 | 24.2 |

The use of the safening agents of the invention in a mixture with acetanilide herbicides is illustrated by the following example.

EXAMPLE 3

A good grade of top soil is placed in a plastic pot and compacted to a depth of approximately 1.27 cm. from the top of said pot. A predetermined number of crop seeds and weed seeds are placed on top of the oil. A cover layer, approximately 1.27 cm., is placed on top of said seeds. The soil is then treated with a mixture of the safening agent, which is 2-(3,4,5,6-tetrachloro-2-pyridylthio)pyridine-N-oxide, and alachlor dispersed or dissolved in a suitable solvent. For each test series, pots are treated with only the herbicide. Additionally, pots are treated with only the safening agent. The herbicidal effect is observed approximately 21 days after treatment. Results are shown below in Table II of 4 tests.

TABLE II

| Herbicide Rate (kg/ha) | Safening Agent Rate (kg/ha) | Percent Inhibition | | | |
|---|---|---|---|---|---|
| | | Sorghum | Green Foxtail | Crabgrass | Barnyard Grass |
| TEST 1 | | | | | |
| 0.035 | 0 | 0 | 98 | 93 | 99 |
| 0.14 | 0 | 33 | 100 | 99 | 100 |
| 0.56 | 0 | 50 | 100 | 99 | 100 |
| 2.24 | 0 | 95 | 100 | 100 | 100 |
| 0 | 0.56 | 0 | 0 | 0 | 0 |
| 0.035 | 0.56 | 0 | 99 | 99 | 97 |
| 0.14 | 0.56 | 15 | 99 | 100 | 99 |
| 0.56 | 0.56 | 45 | 100 | 100 | 99 |
| 2.24 | 0.56 | 93 | 100 | 100 | 100 |
| TEST 2 | | | | | |
| 0.035 | 0 | 0 | 83 | 17 | 96 |
| 0.14 | 0 | 32 | 97 | 70 | 98 |
| 0.56 | 0 | 77 | 99 | 97 | 99 |
| 2.24 | 0 | 92 | 99 | 98 | 100 |
| 0 | 0.56 | 0 | 0 | 0 | 0 |
| 0.035 | 0.56 | 0 | 78 | 15 | 93 |
| 0.14 | 0.56 | 5 | 99 | 63 | 99 |
| 0.56 | 0.56 | 33 | 99 | 98 | 100 |
| 2.24 | 0.56 | 58 | 100 | 100 | 100 |
| TEST 3 | | | | | |
| 0.035 | 0 | 0 | 88 | 23 | 83 |
| 0.14 | 0 | 68 | 98 | 40 | 99 |
| 0.56 | 0 | 93 | 99 | 83 | 100 |
| 2.24 | 0 | 98 | 100 | 99 | 100 |
| 0 | 0.56 | 0 | 10 | 0 | 28 |
| 0.035 | 0.56 | 0 | 85 | 18 | 93 |
| 0.14 | 0.56 | 0 | 97 | 55 | 100 |
| 0.56 | 0.56 | 23 | 99 | 88 | 100 |
| 2.24 | 0.56 | 85 | 100 | 99 | 100 |
| TEST 4 | | | | | |
| 0.035 | 0 | 0 | 90 | 48 | 75 |
| 0.14 | 0 | 28 | 95 | 88 | 95 |
| 0.56 | 0 | 80 | 97 | 95 | 98 |
| 2.24 | 0 | 99 | 99 | 99 | 100 |
| 0 | 0.14 | 0 | 0 | 0 | 0 |
| 0.035 | 0.14 | 0 | 80 | 20 | 48 |
| 0.14 | 0.14 | 10 | 95 | 78 | 98 |
| 0.56 | 0.14 | 35 | 99 | 93 | 99 |

TABLE II-continued

| Herbicide Rate (kg/ha) | Safening Agent Rate (kg/ha) | Percent Inhibition | | | |
|---|---|---|---|---|---|
| | | Sorghum | Green Foxtail | Crab-grass | Barnyard Grass |
| 2.24 | 0.14 | 75 | 100 | 97 | 99 |
| 0 | 0.56 | 0 | 13 | 3 | 5 |
| 0.035 | 0.56 | 0 | 75 | 15 | 35 |
| 0.14 | 0.56 | 8 | 93 | 75 | 88 |
| 0.56 | 0.56 | 23 | 98 | 93 | 100 |
| 2.24 | 0.56 | 78 | 99 | 99 | 99 |
| 0 | 2.24 | 0 | 38 | 28 | 78 |
| 0.035 | 2.24 | 0 | 95 | 33 | 93 |
| 0.14 | 2.24 | 8 | 88 | 38 | 83 |
| 0.56 | 2.24 | 20 | 97 | 83 | 98 |
| 2.24 | 2.24 | 80 | 99 | 98 | 100 |

EXAMPLE 4

The procedure of Example 3 is repeated utilizing seven different sorghum hybrids. Results are summarized below in Table III.

terms of percent inhibition of each seed lot are recorded. For each test, pots are prepared with soil covering the seed containing only acetanilide herbicide. For each series of tests, the herbicidal effect of the safening agent is observed from pots treated with only the safening agent. Results are summarized below in Table IV.

TABLE IV

| Herbicide | Herbicide Rate (kg/ha) | Safening Agent | Safening Agent Rate (kg/ha) | Percent Inhibition of Sorghum |
|---|---|---|---|---|
| Alachlor | 0.56 | — | 0 | 88 |
| " | 4.48 | — | 0 | 99 |
| " | 0.56 | 2-(3,4,5,6-tetrachloro-2-pyridyl-thio)pyridine-N-oxide | 8.96 | 35 |
| " | 4.48 | | 8.96 | 75 |
| Butachlor | 1.12 | — | 0 | 30 |
| " | 8.96 | — | 0 | 85 |
| " | 1.12 | 2-(3,4,5,6-tetrachloro- | 8.96 | 15 |
| " | 8.96 | | 8.96 | 63 |

TABLE III

| Herbicide Rate (kg/ha) | Safening Agent Rate (kg/ha) | Percent Inhibition/Sorghum Hybrid | | | | | | | Percent Weed Inhibition | | | | |
|---|---|---|---|---|---|---|---|---|---|---|---|---|---|
| | | Surgro | Co-op | Northrup-King Mini Milo 52 | Northrup-King 222G | Nebraska Common +70X | Pioneer 894 | Pioneer 8442 | Crab-grass | Foxtail | Barnyard Grass | Pig-weed | Panicum |
| 0.07 | 0 | 42 | 27 | 63 | 33 | 40 | 18 | 18 | 20 | 58 | 93 | 18 | 73 |
| 0.14 | 0 | 67 | 43 | 72 | 63 | 65 | 38 | 37 | 33 | 58 | 96 | 37 | 83 |
| 0.28 | 0 | 78 | 57 | 77 | 73 | 77 | 52 | 57 | 37 | 73 | 97 | 33 | 88 |
| 0.56 | 0 | 92 | 77 | 85 | 80 | 88 | 77 | 77 | 60 | 93 | 97 | 69 | 98 |
| 1.12 | 0 | 88 | 87 | 97 | 90 | 87 | 88 | 90 | 73 | 98 | 98 | 70 | 98 |
| 2.24 | 0 | 97 | 95 | 96 | 94 | 93 | 94 | 93 | 85 | 99 | 99 | 68 | 99 |
| 0 | 0.14 | 0 | 0 | 0 | 0 | 0 | 0 | 0 | 0 | 0 | 0 | 0 | 0 |
| 0.07 | 0.14 | 0 | 0 | 0 | 5 | 0 | 0 | 0 | 23 | 65 | 95 | 10 | 80 |
| 0.14 | 0.14 | 0 | 0 | 0 | 0 | 0 | 0 | 0 | 25 | 55 | 97 | 23 | 83 |
| 0.28 | 0.14 | 25 | 15 | 15 | 15 | 10 | 3 | 10 | 33 | 73 | 97 | 33 | 90 |
| 0.56 | 0.14 | 43 | 23 | 50 | 33 | 45 | 30 | 25 | 50 | 65 | 92 | 45 | 90 |
| 1.12 | 0.14 | 63 | 38 | 60 | 53 | 78 | 33 | 33 | 70 | 85 | 97 | 45 | 97 |
| 2.24 | 0.14 | 78 | 78 | 98 | 85 | 78 | 83 | 88 | 83 | 99 | 100 | 60 | 100 |
| 0 | 0.56 | 0 | 0 | 0 | 0 | 0 | 0 | 0 | 0 | 0 | 0 | 0 | 0 |
| 0.07 | 0.56 | 0 | 10 | 0 | 0 | 0 | 5 | 0 | 35 | 75 | 97 | 30 | 65 |
| 0.14 | 0.56 | 0 | 3 | 5 | 0 | 0 | 0 | 0 | 50 | 70 | 90 | 48 | 80 |
| 0.28 | 0.56 | 8 | 3 | 10 | 10 | 13 | 0 | 13 | 45 | 78 | 93 | 33 | 85 |
| 0.56 | 0.56 | 25 | 23 | 20 | 23 | 30 | 13 | 15 | 43 | 85 | 95 | 40 | 88 |
| 1.12 | 0.56 | 45 | 50 | 83 | 60 | 48 | 35 | 45 | 73 | 97 | 97 | 85 | 93 |
| 2.24 | 0.56 | 75 | 70 | 90 | 85 | 78 | 78 | 83 | 68 | 97 | 100 | 80 | 98 |
| 0 | 2.24 | 0 | 0 | 0 | 0 | 0 | 0 | 3 | 0 | 0 | 0 | 0 | 0 |
| 0.07 | 2.24 | 0 | 0 | 0 | 0 | 0 | 0 | 0 | 38 | 65 | 80 | 15 | 65 |
| 0.14 | 2.24 | 0 | 0 | 0 | 0 | 0 | 0 | 0 | 43 | 78 | 83 | 53 | 73 |
| 0.28 | 2.24 | 10 | 5 | 0 | 3 | 8 | 5 | 0 | 45 | 60 | 92 | 58 | 83 |
| 0.56 | 2.24 | 13 | 8 | 8 | 8 | 18 | 13 | 13 | 55 | 85 | 90 | 80 | 94 |
| 1.12 | 2.24 | 33 | 30 | 58 | 28 | 45 | 38 | 35 | 68 | 85 | 95 | 63 | 93 |
| 2.24 | 2.24 | 75 | 55 | 90 | 70 | 73 | 45 | 50 | 65 | 94 | 90 | 78 | 95 |

EXAMPLE 5

A good grade of top soil is placed in a container and compacted to a depth of approximately 1.27 cm. from the top of said container. A predetermined number of sorghum seeds to be tested are placed on top of the soil. A quantity of soil sufficient to substantially fill the container is measured and placed in a second container. A measured quantity of the safening agent dispersed or dissolved in a suitable carrier is applied to the soil in the second container. A measured quantity of the acetanilide herbicide dispersed or dissolved in a suitable carrier is then applied to the soil already treated with the safening agent. The soil containing the safening agent and herbicide is thoroughly mixed. The seeds are covered with the soil containing the safening agent and acetanilide herbicide and the pots are leveled. The pots are then placed on a sand bench in the greenhouse and watered from below as needed. The plants are observed at the end of approximately 21 days and the results in

| | | 2-pyridyl-thio)pyri-dine-N-oxide | | |
|---|---|---|---|---|
| 2-chloro-N-(2-methoxy-1-methylethyl)-6'-ethyl-o-acetotoluidide | 0.56 | — | 0 | 50 |
| | 4.48 | — | 0 | 97 |
| " | 0.56 | 2-(3,4,5,6-tetrachloro-2-pyridyl-thio)pyridine-N-oxide | 8.96 | 25 |
| " | 4.48 | | 8.96 | 70 |

As noted above, crop plants may be protected from herbicidal activity by treating the crop seed with the safening agent prior to planting. Example 6 illustrates such activity.

EXAMPLE 6

Sorghum seeds are treated with a solution of 2-(2,4,5,6-tetrachloro-2-pyridylthio)pyridine-N-oxide in dichloromethane. The solvent was evaporated which left only the safening agent on the seed. Untreated and treated sorghum seeds were planted in pots. Selected weed species were planted in separate pots. 1.27 cm. deep soil cover layer was placed on the pre-seeded pots. The soil surface was then treated with the herbicide. Approximately 21 days later, the results were observed and recorded. Table V, below, summarizes the results observed when tests were conducted in accordance with Example 6.

TABLE V

| Herbicide | Herbicide Rate (kg/ha) | Percent Sorghum Inhibition Seed Treatment Concentration (Grams of Safening Agent/Kilograms of Seed) | | | |
|---|---|---|---|---|---|
| | | 0 | 0.6 | 2.5 | 10 |
| Alachlor | 0.07 | 3 | 0 | 0 | 0 |
| Alachlor | 0.14 | 25 | 0 | 0 | 0 |
| Alachlor | 0.28 | 73 | 35 | 15 | 5 |
| Alachlor | 0.56 | 75 | 40 | 30 | 20 |
| Alachlor | 1.12 | 95 | 83 | 75 | 65 |
| Alachlor | 2.24 | 97 | 85 | 68 | 63 |
| 2-Chloro-N-(2-methoxy-1-methyl-ethyl)-6'-ethyl-o-acetotoluidide | 0.07 | 0 | 0 | 0 | 0 |
| | 0.14 | 0 | 0 | 0 | 0 |
| | 0.28 | 0 | 0 | 0 | 0 |
| | 0.56 | 63 | 28 | 30 | 25 |
| | 1.12 | 93 | 70 | 38 | 28 |
| " | 2.24 | 97 | 88 | 58 | 43 |

As noted, selected weed species were planted as a control to determine the efficiency of the herbicide. At rates between 0.14 kilograms per hectare and 0.56 kilograms per hectare, weed inhibition ranged from 63 to 100 percent for alachlor and from 57 to 99 percent for 2-chloro-N-(2-methoxy-1-methylethyl)-6'-ethyl-o-acetotoluidide.

The above examples illustrate that the 2-(pyridylthio)pyridine-N-oxides of the present invention are useful in reducing herbicidal injury to crop plants, especially sorghum. The safening agents may be applied to the plant locus as a mixture, i.e., a mixture of a herbicidally effective amount of acetanilide herbicide and a safening effective amount of safening agent, or sequentially, i.e., the plant locus may be treated with an effective amount of the herbicide followed by a treatment with the safening agent or vice versa. The ratio of herbicide to safening agent may vary depending upon the crop to be protected, weeds to be inhibited, herbicide used, etc., but normally a herbicide to safening agent ratio ranging from 1:25 to 25:1 (perferably 1:5 to 5:1) parts by weight may be employed.

The herbicide, safening agent or mixture thereof may be applied to the plant locus alone or the herbicide, safening agent or mixture thereof may be applied in conjunction with a material referred to in the art as an adjuvant in liquid or solid form. Mixtures containing the appropriate herbicide and safening agent usually are prepared by admixing said herbicide and safening agent with an adjuvant including diluents, extenders, carriers and conditioning agents to provide compositions in the form of finely-divided particulate solids, granules, pellets, wettable powders, dusts, solutions and aqueous dispersions or emulsions. Thus, the mixture may include an adjuvant such as a finely-divided particulate solid, a solvent liquid of organic origin, water, a wetting agent, dispersing agent, or emulsifying agent or any suitable combination of these.

When applying the herbicide, safening agent or mixture thereof to the plant locus, useful finely-divided solid carriers and extenders include, for example, the talcs, clays, pumice, silica, diatomaceous earth, quartz, Fullers earth, sulfur, powdered cork, powdered wood, walnut flour, chalk, tobacco dust, charcoal and the like. Typical liquid diluents useful include for example, Stoddard solvent, acetone, alcohols, glycols, ethyl acetate, benzene and the like. Such compositions, particularly liquids and wettable powders, usually contain as a conditioning agent one or more surface-active agents in amounts sufficient to render a given composition readily dispersible in water or in oil. By the term "surface-active agent", it is understood that wetting agents, dispersing agents, suspending agents and emulsifying agents are included therein. Such surface-active agents are well known and reference is made to U.S. Pat. No. 2,547,724, Columns 3 and 4, for detailed examples of the same.

Compositions of this invention generally contain from about 5 to 95 parts herbicide and safening agent, about 1 to 50 parts surface-active agent and about 4 to 94 parts solvent, all parts being by weight based on the total weight of the composition.

The application of the herbicide, safening agent or mixture thereof in a liquid or particulate solid form can be carried out by conventional techniques utilizing, for example, spreaders, power dusters, boom and hand sprayers, spray dusters and granular applications. The compositions can also be applied from airplanes as a dust or spray. If desired, application of the compositions of the invention to plants can be accomplished by incorporating the compositions in the soil or other media.

The above examples also illustrate that the crop may be protected by treating the crop seed with an effective amount of safening agent prior to planting. Generally, small amounts of safening agent are required to treat such seeds. Table V illustrates that a weight ratio of as little as 0.6 parts of safener per 1000 parts of seed may be effective. The amount of safener utilized in treating the seed may be increased if desired. Generally, however, a weight ratio of safening agent to seed weight may range from 0.1 to 10.0 parts of safening agent per 100 parts of seed. The determination of the effective amount of safening agent required is well within the skill of the art.

Since only a very small amount of active safening agent is usually required for the seed treatment, the compound preferably is formulated as a powder or an emulsifiable concentrate which can be diluted with water by the seed treater for use in the seed treating apparatus. Of course, under certain conditions, it may be desirable to dissolve the safening agent in an organic solvent for use as a seed treatment or the pure compound alone may be used under properly controlled conditions.

There are thus also provided by this invention novel seed treating compositions containing one or more of the described active safening agents intimately dispersed in an inert carrier or diluent for the intended use. Such carriers may be either solids, such as talc, clay, diatomaceous earth, sawdust, calcium carbonate and the like or liquids such as water, kerosene, acetone, benzene, toluene, xylene, and the like in which the active agent may be either dissolved or dispersed. Emulsifying agents are advisably used to achieve a suitable emulsion if two immiscible liquids are used as a carrier. Wetting agents may also be used to aid in dispersing the active safening agent in liquids used as a carrier in which the agent is not completely soluble. Emulsifying agents and wetting agents are sold under numerous tradenames and may be either pure compounds, mixtures of compounds of the same general groups, or they may be mixtures of compounds of different classes. Typical satisfactory surface-active agents which may be used are alkali metal higher alkylarylsulfonates such as sodium dodecylbenzenesulfonate and the sodium salts of alkylnaphthalenesulfonic acids, fatty alcohol sulfates such as the sodium salts of monoesters of sulfuric acid with n-aliphatic alcohols containing 8–18 carbon atoms, long chain quaternary ammonium compounds, sodium salts or petroleum-derived alkylsulfonic acids, polyethylene sorbitan monooleate, alkylaryl polyether alcohols, water-soluble lignin sulfonate salts, alkalicasein compositions, long chain alcohols usually containing 10–18 carbon atoms, and condensation products of ethylene oxide with fatty acids, alkylphenols and mercaptans.

Preferably, the compounds of the invention are 2-(pyridylthio)pyridine-N-oxides in which the pyridyl moiety is substituted with at least one halogen atom. To clarify, the preferred compounds have the structure

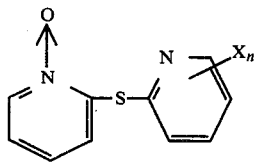

wherein X is halogen and n is 1, 2, 3 or 4. Most preferably, X is chloro and n is 4.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A method of reducing injury to sorghum crop plants due to the application thereto of α-haloacetanilide herbicide which comprises applying to the plant locus a safening effective amount of a compound having the formula

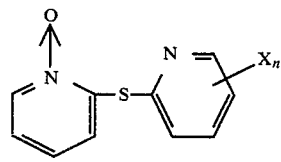

wherein X is halogen and n is 4.

2. A method according to claim 1 wherein X is chloro.

3. A method for reducing herbicidal injury to sorghum crop plants which comprises applying to the plant locus an effective amount of a mixture comprising a herbicidally effective amount of an α-haloacetanilide herbicide and a safening effective amount of a compound having the formula

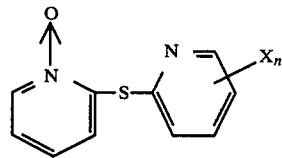

wherein X is halogen and n is 4.

4. A method according to claim 3 wherein X is chloro.

5. A method for reducing herbicidal injury to sorghum by application thereto of an α-haloacetanilide herbicide which comprises coating the seed of a sorghum plant with a safening effective amount of a compound having the formula

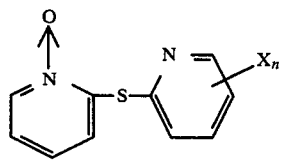

wherein X is halogen and n is 4.

6. A method according to claim 5 wherein X is chloro.

7. A mixture which comprises a herbicidally effective amount of an α-haloacetanilide herbicide and a safening effective amount of a compound having the formula

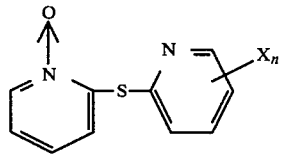

wherein X is halogen and n is 4.

8. A mixture according to claim 7 wherein X is chloro.

9. A mixture according to claim 7 wherein said herbicide is alachlor.

10. A mixture according to claim 7 wherein said herbicide is 2-chloro-N-(2-methoxy-1-methylethyl)-6'-ethyl-o-acetotoluidide.

11. Sorghum, seed bearing thereon a coating of a safening effective amount of a compound having the formula:

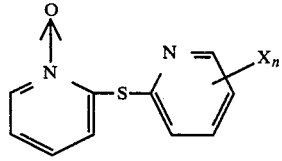

wherein X is halogen and n is 4.

12. Seed according to claim 11 wherein said compound is one in which X is chloro.

* * * * *